United States Patent
Torres-Suarez et al.

(10) Patent No.: US 9,173,925 B2
(45) Date of Patent: Nov. 3, 2015

(54) FERRIMANNITOL-OVALBUMIN TABLET COMPOSITION

(75) Inventors: Ana Isabel Torres-Suarez, Madrid (ES); Daniel Filipe Tavares Da Silva Fernandes, Madrid (ES); Maria Esther Gil Alegre, Madrid (ES)

(73) Assignee: Tedec Meiji Farma, S.A., Madrid (ES)

( * ) Notice: Subject to any disclaimer, the term of this patent is extended or adjusted under 35 U.S.C. 154(b) by 17 days.

(21) Appl. No.: 13/810,346

(22) PCT Filed: Jul. 14, 2011

(86) PCT No.: PCT/EP2011/062022
§ 371 (c)(1),
(2), (4) Date: Feb. 11, 2013

(87) PCT Pub. No.: WO2012/007538
PCT Pub. Date: Jan. 19, 2012

(65) Prior Publication Data
US 2013/0143819 A1 Jun. 6, 2013

(30) Foreign Application Priority Data
Jul. 15, 2010 (EP) .................................. 10382196

(51) Int. Cl.
*A61K 38/38* (2006.01)
*A61K 9/00* (2006.01)
*A61K 9/20* (2006.01)
*A61K 33/26* (2006.01)

(52) U.S. Cl.
CPC ............. *A61K 38/38* (2013.01); *A61K 9/0056* (2013.01); *A61K 9/2018* (2013.01); *A61K 9/2027* (2013.01); *A61K 9/2054* (2013.01); *A61K 33/26* (2013.01)

(58) Field of Classification Search
CPC .................................................. A61K 38/38
See application file for complete search history.

(56) References Cited

U.S. PATENT DOCUMENTS

| 2003/0190355 A1 | 10/2003 | Hermelin et al. | |
| 2010/0286286 A1* | 11/2010 | Ikeda et al. | 514/770 |
| 2010/0330150 A1* | 12/2010 | Venkatesh et al. | 424/439 |

FOREIGN PATENT DOCUMENTS

| EP | 0875249 A | 4/1998 | |
| EP | 1655308 A | 5/2006 | |
| EP | 1 944 017 A2 * | 7/2008 | ............... A61K 9/20 |

OTHER PUBLICATIONS

Gutierrez, Magnetic and structural study of the state of iron in the oral haematinic ferrimannitol ovoalbumin, Journal of Inorganic Biochemistry 100:413-417, 2006.*
Gonzalez-Penas et al., 1998, Bioavailability of the iron formulated as natural ferric protein (TM/FMOA) and natural ferric protein + folic acid (TM/FMOA+FOL), Eur J Drug Metab Pharmacokinet, 23(2): 213-217.*
International Search Report dated Aug. 31, 2011 for PCT/EP2011/062022.
Profer granulado 40 mg, Jul. 1, 1991, Retrieved from the Internet, http://www.vademecum.es/medicamento-profer_3279 (viewed Apr. 11, 2013).
Gutierrez et al., Magnetic and structural study of the state of iron in the oral haematinic ferrimannitol ovoalbumin. Journal of Inorganic Biochemistry 100 (2006) 413-417.
Zlotkin et al., Micronutrientr Sprinkles to Control Childhood Anaemia. Plos Med , Jan. 2005, vol. 2, Issue 1, e10, e1, 0024-0028.
Fernandez et al., Rapid Development and Optimization of Tablet Manufacturing Using Statistical Tools, AAPS PharmSciTech, vol. 9, No. 2, Jun. 2008, 620-627.
Conrad et al., Pathways of Iron Absorption. Blood Cells, Molecules, and Diseases (2002) 29(3) Nov./Dec.: 336-355.
Szabo-Revesz et al., Development of spherical iron (II) sulfate heptahydrate-containing solid particles with sustained drug release. European Journal of Pharmaceutics and Biopharmaceutics 66 (2007) 193-199.

* cited by examiner

*Primary Examiner* — Amber D Steele
(74) *Attorney, Agent, or Firm* — Kramer Amado, P.C.

(57) ABSTRACT

The invention refers to an oral pharmaceutical tableted dosage form which comprises a mixture of: a) granules comprising ferrimannitol-ovalbumin (FMOA) and at least an intragranular pharmaceutical acceptable excipient including a binder; and b) extragranular pharmaceutical excipients including a filler and a binder; which may be obtained by wet-granulation and compression.

26 Claims, No Drawings ferrimannitol-ovalbumin tablet composition

FIELD OF THE INVENTION

The present invention relates to new solid dosage forms containing ferrimannitol-ovalbumin (FMOA) and a process for elaborating them.

BACKGROUND

Ferrimannitol-ovalbumin (FMOA) is an adduct between ovalbumin and the complex Fe(III)-mannitol, useful as drug substance to correct haematological variables modified by loss and shortage of iron. There are various processes disclosed in the prior art for the preparation of this substance.

EP 0 875 249 B1 discloses a process for preparing complexes consisting of Fe(III), a polyhydroxylate compound and ovalbumin such as FMOA (see example 1).

Likewise, EP 1 655 308 B1 describes a procedure to obtain adducts of soluble ovalbumin with trivalent iron polyalcohol complexes comprising the treatment of ovalbumin with an alkaline protease which allows the elimination of the allergy and immunotoxicity problems associated with said albumin. Example 1 of EP 1 655 308 B1 is directed to FMOA.

The formulation of FMOA into a pharmaceutical composition entails several inconveniences. Firstly, as it is known, Fe has a distinctive metallic unpleasant taste that makes difficult to elaborate liquid dosage forms for oral administration well accepted by the patients. This unpleasant taste could be avoided with solid dosage forms, by either using excipients (e.g. flavors) to mask the iron taste and/or administering the same without their previous disintegration or dissolution. However, such forms would be hard to swallow because of their size. Furthermore, the FMOA is a dark-red, homogeneous substance with appearance of powder or of flakes, difficult to formulate as a solid dosage form, so that to date it has not been possible to obtain oral formulations in the form of tablets in a reliable and robust way.

FMOA is currently marketed for the treatment of ferropenic anemia and iron deficiency states exclusively as a granular composition which has to be dissolved in water: for instance, each sachet containing 600 mg of composition is poured into 200 ml of water and stirred until complete dissolution; the solution must be immediately consumed. As FMOA is usually prescribed to pregnant women, the intake of a granular formulation dissolved in water most often gives place to emetic events in this patient group. It is readily appreciated in this regard that a dosage form easy to intake and with pleasant taste would be essential with the aim of avoiding emesis in patients susceptible to emesis.

Accordingly, there is still a need to find a solid dosage form of ferrimannitol-ovalbumin useful as therapeutic for iron-deficiency anaemia and other related states that solve at the same time at least one of the problems associated with the formulations disclosed in the state of the art. Preferably, the pharmaceutical dosage formulation containing FMOA should show the following characteristics:

pleasant taste;
easy to intake;
proper dosage uniformity; and
robust manufacturing process.

BRIEF DESCRIPTION OF THE INVENTION

The inventors of the present invention have surprisingly found that it is possible to formulate FMOA in the form of tablets. This new pharmaceutical dosage form of FMOA for oral administration is elaborated by a robust manufacturing process which provides high uniformity of dosage. Further, the tablets of the invention can be designed to achieve a fast disintegration and/or dissolution in water before being taking and/or directly in the mouth, so that a solution with pleasant taste is formed, thus making easier the intake.

Therefore, one aspect of the present invention relates to an oral pharmaceutical tableted dosage form which comprises a mixture of:
  a) granules comprising ferrimannitol-ovalbumin (FMOA) and at least an intragranular pharmaceutical acceptable excipient including a binder; and
  b) extragranular pharmaceutical excipients including a filler and a binder.

Optionally, the oral pharmaceutical tableted dosage form further comprises a coating. Examples of coated tablets are sugar-coated tablets or film-coated tablets.

In preferred embodiments of the invention, the tablets are chewable or soluble/dispersible in a little amount of water; more preferably they are orodispersible (orally disintegrating tablets) providing a fast disintegration and/or dissolution in the mouth.

Another aspect of the invention refers to a process for preparing the above-mentioned composition comprising:
  i) granulating by wet granulation FMOA and at least an intragranular pharmaceutical acceptable excipient including a binder;
  ii) blending the granule obtained with extragranular pharmaceutical excipients including a filler and a binder;
  iii) compressing the mixture obtained in the previous step into a tablet; and
  iv) optionally, coating the tablet obtained in the previous step.

In addition to a binder, other suitable intragranular pharmaceutical excipients may be used such as fillers or superdisintegrants.

Another aspect of this invention refers to a pharmaceutical composition obtainable by the process defined above.

Another aspect of this invention refers to a pharmaceutical composition as defined above for use in the treatment and/or prophylaxis of iron-deficiency states.

Another aspect of this invention refers to the use of a pharmaceutical composition as defined above in the manufacture of a medicament for the treatment and/or prophylaxis of iron-deficiency states.

Another aspect of the present invention refers to a method for the treatment and/or prophylaxis of iron-deficiency states, said method comprising administering to the subject in need of such a treatment or prophylaxis a pharmaceutical composition as defined above containing a therapeutically effective amount of ferrimannitol-ovalbumin (FMOA).

Iron-deficiency states include iron-deficiency anemia, ferropenic anemia as well as other conditions involving iron-deficiency such as achlorhydria, gastrectomy, burns, excessive blood loss, hemorrhages, renal disease and bowel diseases.

These aspects and preferred embodiments thereof are additionally also defined in the claims.

DETAILED DESCRIPTION OF THE INVENTION

In order to facilitate the comprehension of the present invention, the meanings of some terms and expressions as used in the context of the invention are included herein.

The term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "excipient" refers to a carrier, adjuvant or vehicle with which FMOA is administered and include any such materials known in the art that are nontoxic and do not interact with other components of a pharmaceutical composition. Suitable pharmaceutical excipients are described in "Remington's Pharmaceutical Sciences" by E. W. Martin. As used herein, the term "intragranular" refers to an excipient forming part of the granules of the pharmaceutical composition. Likewise, as used herein, the term "extragranular" refers to an excipient not forming part of the granules, i.e., an excipient added to the composition once the granules have been obtained.

By an "effective" amount or a "therapeutically effective amount" is meant a nontoxic but sufficient amount of FMOA ($Fe^{3+}$) to provide the desired effect. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation. In general, amounts of FMOA equivalent to about at least 40 mg of $Fe^{3+}$ are found to be therapeutically effective.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Unless otherwise stated, all amounts are expressed as percentage by weight with respect to the weight of the formulation.

As noted in the background section, the preparation of pharmaceutical compositions of ferrimannitol-ovalbumin (FMOA) represents a real challenge due to the particular properties of this active ingredient. For instance, its metallic unpleasant taste prevents FMOA to be formulated in liquid dosage form. Solid dosage forms are not easily accessible either since the handling of solid FMOA is complicated. Lack of flowability of the mixture final as well as lack of uniformity, capping, laminating and sticking to punches in the tablets are usual problems found for FMOA in the tabletting machine. In fact, the design of solid dosage forms is limited so far to granular compositions to be dissolved in water.

The inventors, after extensive research, have attained a reliable and robust process for preparing tablets of FMOA, a more appropriate dosage form for patients susceptible to emesis such as pregnant women.

The process provided by the present invention for preparing tablets of FMOA involves a pre-treatment of wet granulation prior to the compression step. More concretely, the process comprises the following steps:
i) granulating by wet granulation FMOA and at least an intragranular pharmaceutical acceptable excipient including a binder;
ii) blending the granules obtained with extragranular pharmaceutical excipients including a filler and a binder;
iii) compressing the mixture obtained in the previous step into a tablet; and
iv) optionally, coating the tablet obtained in the previous step.

i) Granules Elaboration

The granules are elaborated by mixing FMOA with pharmaceutically acceptable excipients (intragranular). FMOA should be present in a therapeutically effective amount. The amount of FMOA in the composition typically ranges from about 20% to 30% by weight. Preferably, the tablets are designed to comprise an amount of FMOA equivalent to about 40 mg of $Fe^{3+}$.

The skilled in the art will readily determine by routine experimentation the appropriate intragranular excipients depending upon the desired final tablet. The intragranular excipients may help to impart satisfactory compression characteristics to the formulation and, without being bound to any particular theory, it is believed that the dissolving/disintegrating properties of the final tablet will be determined to a great extent by the intragranular excipients.

In general, it is convenient to use fillers (diluents) to increase the bulk and reach a practical size for compression. Examples of fillers suitable as intragranular excipients include, but are not limited to, compressible sugar, dextrates, dextrin, dextrose, lactose, mannitol, sorbitol, microcrystalline cellulose, silicified microcrystalline cellulose, etc. The combination of above-mentioned fillers can also be used. Mannitol is a particularly preferred filler in the present invention. Further, the filler is conveniently used in an amount of from about 15% to 40% by weight.

Certain fillers, such as mannitol, lactose, sorbitol, sucrose, and inositol, could be added to permit disintegration in the mouth by chewing (thus forming chewable tablets). Upon chewing, properly prepared tablets will disintegrate smoothly at a satisfactory rate, have a pleasant taste and feel, and leave no unpleasant metallic aftertaste in the mouth. If a filler is used to achieve a chewable tablet, it should be preferably employed in an amount from about 50 to 55% to 80 to 85% by weight.

Further, with the aim of preparing water-soluble/dispersible tablets (e.g. orodisersible), FMOA may be mixed with a filler (like those cited above) and a superdisintegrant with swelling capabilities. As used herein, the terms "disintegrant" and "superdisintegrant" are interchangeable. Examples of superdisintegrants suitable as intragranular excipients include, but are not limited to, calcium croscarmellose, sodium croscarmellose, crosslinked PVP (crospovidone, polyplasdone or kollidon XL), sodium starch glycolate, etc. The combination of above-mentioned superdisintegrants can also be used. Croscarmellose is a particularly preferred superdisintegrant in the present invention. Further, the superdisintegrant is conveniently used in an amount of from about 2% to 6% by weight or from about 2% to 8% by weight.

In a preferred embodiment of the invention, mannitol is employed as filler and sodium croscarmellose as superdisintegrant. Such combination is especially convenient to obtain a rapid disintegration and/or dissolution of the tablet in a bit of water or in the mouth (orodispersible tablet). The preferred ratios between filler and superdisintegrant are from about 85:15 to about 70:30 by weight Next, the obtained mixture must be wet with a granulating fluid including a binder to obtain a wet powder. The granulating fluid contains a solvent which must be volatile so that it can be easily removed by drying, and be non-toxic (e.g. water, ethanol, isopropanol, either alone or in combination). Preferably, the fluid is an aqueous based liquid solution, since aqueous solutions have the advantage of being safer to deal with than solvents.

Examples of binders include, but are not limited to, starches, microcrystalline cellulose, povidone, hydroxypropyl cellulose, hydroxyethyl cellulose and hydroxypropylmethyl cellulose, etc. The combination of above-mentioned binders can also be used. The preferred binders according to the invention are povidone and hydroxypropyl cellulose. Further, the binder is preferably used in an amount of from about 0.5% to 5% by weight or from about 0.5% to 8% by weight.

The wet powder is dried until the solvent content in the powder is minimal (preferably, about 5% w/w at most), to obtain a first particulate mixture. The temperature to attain an effective drying depends on each solvent. For instance, when water is used as solvent of the granulating fluid, the drying process is carried out suitably above room temperature, preferably at from 35° C. to 45° C. and it usually proceeds in less than 18 h, thus affording a water content equal or below 5% w/w.

Finally, said first particulate mixture is sieved to obtain a well defined particle size range. From about 0.8 to 1.2 mm screens (e.g. 1 mm) are suitable to sieve the mixture. It is preferred that the size of the particles ranges from about 63 to 710 μm.

The granules may be obtained by using conventional equipments such as high shear mixer-granulators, fluid-bed granulators, one pot granulators, etc.

ii) Final Blend Elaboration

In this step, the granules of well defined particle size previously obtained are mixed with pharmaceutically acceptable excipients (extragranular) to obtain a second particulate mixture. Without being bound to any particular theory, it is believed that the extragranular excipients will be important with respect to the taste, flowability, compressibility, hardness and friability, but also affecting to the disintegration and dissolution of the final tablet.

According to the present invention, at least a filler and a binder are used as extraganular excipients. Examples of fillers and binders suitable as extragranular excipients include those mentioned above within the granule elaboration. These additives as extragranular excipients are preferably present in an amount from about 40% to 70% by weight.

In a preferred embodiment, the filler is derived from a poliol such as mannitol, lactose, sorbitol, sucrose, and inositol since they give pleasant taste to the formulation apart from good flowability properties. The most preferred extragranular filler in the present invention is mannitol. Further, the extragranular filler is preferably present in amounts ranging from about 40% to 60% by weight.

Improved compressibility, robustness of the compression step and tablet hardness avoiding sticking and capping problems may be obtained using hydroxypropyl cellulose (HPC) as direct compression binder. Further, the extragranular binder is preferably present in amounts ranging from about 2% to 8% by weight.

Other excipients that may be used to be mixed with the granules containing FMOA include sweetening agents, flavors or solubility enhancers, etc.

Examples of sweetening agents include, but are not limited to, saccharin sodium, aspartame, accesulfame, halitame and sucralose.

Examples of flavors include, but are not limited to, vanilla, coffee, caramel, and banana.

In some cases, such as for water-soluble/dispersible tablets (e.g. orodispersible) or chewable tablets, the use of a dissolution enhancer may be helpful. For example, desirable dissolution rate is obtained by adding glycine as dissolution enhancer.

The addition of lubricant agents prior to the compression step helps to prevent sticking of the final mixture to the punches of the tablet machine. Examples of lubricants include, but are not limited to, magnesium stearate, calcium stearate, PEG 6000, sodium stearyl sumarate and sodium lauryl sulphate. The combination of above-mentioned lubricants can also be used. The preferred lubricants are sodium stearyl fumarate and magnesium stearate, more preferably used in combination. The lubricant is preferably used in an amount of from about 0.2% to 2% by weight or from about 0.9% to 3% by weight.

iii) Compression

Once the granules are mixed with appropriate extraganular excipients, the final mixture is tableted, for instance by a rotatory tablet machine under a maximum pre-compression force of about 8 kN and maximum main compression force of about 80 kN. Such a procedure (pre-compression+compression) is convenient in some embodiments.

iv) Coating

The tablets may be coated after being pressed to afford sugar-coated tablets or film-coated tablets.

As noted previously, preferred embodiments of the present invention relate to chewable or dispersible/soluble tablets of FMOA. The term "dispersible" is intended to include the term "soluble" and is used herein according to its common meaning in the pharmaceutical field, that is to say, a tablet which is capable of dispersing in water to provide an homogeneous dispersion which is capable of passing through a sieve screen with a nominal mesh aperture of 710 μm.

In a more preferred embodiment, the tablets of the invention are orodispersible. Orodispersible tablets are also called orally disintegrating tablets (ODTs), quick disintegrating tablets, mouth dissolving tablets, fast disintegrating tablets, fast dissolving tablets, rapid dissolving tablets, porous tablets, and rapimelts.

Of all the above terms, United States pharmacopoeia (USP) approved these dosage forms as ODTs. United States Food and Drug Administration (FDA) defined ODT as "a solid dosage form containing medicinal substance or active ingredient which disintegrates rapidly usually within a matter of seconds when placed upon the tongue." The disintegration time for ODTs generally ranges from several seconds to about a minute.

In the European Pharmacopoeia (Ph.Eur.) 5th edition, Supplement 5.2, published in June 2004, orodispersible tablets are defined as non-coated tablets for placing in the mouth which disintegrate quickly before they are swallowed. It also establishes 3 minutes as the time under which they must disintegrate in the disintegration test for tablets and capsules, according to the Ph. Eur. 2.9.1. method.

As used in the present invention, "orodispersible" and the related terms above listed refers simply to a fast disintegration and/or dissolution in the mouth, preferably within 3 min.

The steps of a particular process for the preparation of water-soluble/dispersible tablets of FMOA, more concretely orodispersible, according to the present invention are defined below:

i) granules elaboration by:
   mixing FMOA 20-30% w/w with mannitol 15-40% w/w and sodium croscarmellose 2-8% w/w;
   wetting the thus obtained mixture with an aqueous liquid with a povidone 0.5-8% w/w to obtain a wet powder;
   drying the thus obtained wet powder until the water content in the powder is at the most about 5% w/w to obtain a first particulate mixture; and
   sieving the thus obtained first particulate mixture to obtain a well defined particle size range.
ii) final blend elaboration by:
   adding mannitol 40-60% w/w and hydroxypropyl cellulose 2-8% w/w to obtain a second particulate mixture; and
   mixing the further obtained mixture with sodium stearyl fumarate 0.5-2% w/w and magnesium stearate 0.4-1% w/w; and
iii) compressing the thus obtained final mixture into tablets.

Another aspect of this invention refers to a pharmaceutical composition obtainable by the processes defined above.

The mentioned formulations will be prepared using standard methods such as those described or referred to in the Spanish and US Pharmacopoeias and similar reference texts.

The following examples are merely illustrative of certain embodiments of the invention and cannot be considered as restricting it in any way.

EXAMPLES

Example 1

Pharmaceutical Process

In a high shear mixer the active pharmaceutical ingredient, the soluble filler and the disintegrant are added and pre-mixed for 5 minutes. After that, the binder dissolved in water is sprayed onto the mixture in a rate of 3 L/minute in order to obtain a wet mass. This wet mass was kneading at least for 5 minutes. This wet mass is dried preferably at from about 35° C. to 45° C. and it usually proceeds in less than 24 h to give granules with LOD<5% (LOD=Loss on Drying). Then this particulate mixture is sieved trough 1 mm sieve, followed by the addition of extragranular excipients at one particular order. First, blending granules with HPC at least 3 minutes. After that, adding glycine, mannitol, saccharin sodium, and a flavour blending at least 10 minutes. Finally, adding lubricants sieving them trough 0.25 mm sieve and blending from 3 to 5 minutes. This final mixture is compressed into tablets in a rotatory tablet machine (Manesty Unipress Diamond 20) with 20 stations, using a oval punch shape (8×21.5 mm diameter) at a weight of 1200 mg.

Tablet Constituents:

|   | Ingredient | %/tablet | Function |
|---|---|---|---|
| Granules | Ferrimannitol-ovalbumin | 23.6% (equal to 40 mg de Fe 3+) | Active substance |
|   | D-Mannitol | 16.6 | Filler/sweetening agent |
|   | Croscarmellose sodium | 3.97 | Disintegrant |
|   | Povidone | 0.7 | Binder |
|   | water |   | Solvent |
| Extragranular | D-mannitol | csp | Filler/sweetening agent |
|   | Glycine | 10 | Solubility enhancer |
|   | Hydroxypropyl cellulose | 4 | Binder |
|   | Saccharin sodium | 1 | Sweetening agent |
|   | Coffee flavor | 0.15 | Flavor |
|   | Magnesium stearate | 0.4 | Lubricant |
|   | Sodium Stearyl Fumarate | 0.8 | Lubricant |

The tablets obtained have a pleasant taste and proper dosage uniformity. Further, these tablets present a hardness higher than 90N, a disintegration time of less than three minutes and a friability below 1%. The behavior of the mixture in the tabletting machine is very good as well since neither laminating nor sticking to punches are detected.

Example 2

Comparative Example

Pharmaceutical Process

In a high shear mixer the active pharmaceutical ingredient, the soluble filler and the disintegrant are added and pre-mixed for 5 minutes. After that, the binder dissolved in water is sprayed onto the mixture in a rate of 3 L/minute in order to obtain a wet mass. This wet mass was kneading at least for 5 minutes. This wet mass is dried preferably at from about 35° C. to 45° C. and it usually proceeds in less than 24 h to give granules with LOD<5%. Then this particulate mixture is sieved trough 1 mm sieve, followed of the addition of extragranular excipients at one particular order. Blending the granules, glycine, mannitol, Saccharin sodium, and a flavour at least 10 minutes. Adding lubricants and blending from 3 to 5 minutes. This final mixture is compressed into tablets in a rotatory tablet machine.

|   | Ingredient | %/tablet | Function |
|---|---|---|---|
| Granules | Ferrimannitol-ovalbumin | 23.6% (equal to 40 mg de Fe 3+) | Active substance |
|   | D-Mannitol | 16.6 | Filler/sweetening agent |
|   | Croscarmellose sodium | 3.97 | Disintegrant |
|   | Povidone | 0.7 | Binder |
|   | water |   | Solvent |
| Extragranular | D-mannitol | csp | Filler/sweetening agent |
|   | Glycine | 10 | Solubility enhancer |
|   | Saccharin sodium | 1 | Sweetening agent |
|   | Coffee flavor | 0.15 | Flavor |
|   | Magnesium stearate | 0.4 | Lubricant |
|   | Sodium Stearyl Fumarate | 0.8 | Lubricant |

These tablets do not contain an extragranular binder. Although they have a pleasant taste and proper dosage uniformity, tablets tend to laminate in the tabletting machine.

The invention claimed is:

1. An orodispersible pharmaceutical tableted dosage form which comprises a mixture of:
   a) granules produced by wet granulation of ferrimannitol-ovalbumin (FMOA), and at least an intragranular pharmaceutically acceptable excipient including an intragranular binder selected from the group consisting of starches, microcrystalline cellulose, povidone, hydroxypropyl cellulose, hydroxyethyl cellulose, hydroxypropylmethyl cellulose and mixtures thereof; and
b) extragranular pharmaceutical excipients including an extragranular filler and an extragranular binder,
wherein the extragranular binder is present in an amount of from about 2% to 8% by weight.

2. The dosage form according to claim 1, wherein the extragranular binder is selected from the group consisting of starches, microcrystalline cellulose, povidone, hydroxypropyl cellulose, hydroxyethyl cellulose, hydroxypropylmethyl cellulose and mixtures thereof.

3. The dosage form according to claim 1, wherein the intragranular binder is present in an amount of from about 0.5% to 5% by weight.

4. The dosage form according to claim 1, wherein the extragranular filler is selected from the group consisting of compressible sugar, dextrates, dextrin, dextrose, lactose, mannitol, sorbitol, sucrose, inositol, microcrystalline cellulose, silicified microcrystalline cellulose and mixtures thereof.

5. The dosage form according to claim 4, wherein the extragranular filler is present in an amount from about 40% to 60% by weight.

6. The dosage form according to claim 4, wherein the extragranular filler is mannitol.

7. The dosage form according to claim 1, wherein the granules further comprise an intragranular filler and a superdisintegrant.

8. The dosage form according to claim 7, wherein the intragranular filler is selected from the group consisting of compressible sugar, dextrates, dextrin, dextrose, lactose, mannitol, sorbitol, sucrose, inositol, microcrystalline cellulose, silicified microcrystalline cellulose and mixtures thereof.

9. The dosage form according to claim 8, wherein the filler is present in an amount of from about 15% to 40% by weight.

10. The dosage form according to claim 7, wherein the superdisintegrant is selected from the group consisting of calcium croscarmellose, sodium croscarmellose, crosslinked PVP and sodium starch glycolate and mixtures thereof.

11. The dosage form according to claim 10, wherein the superdisintegrant is present in an amount of from about 2% to 6% by weight.

12. The dosage form according to claim 1, further comprising a lubricant selected from the group consisting of magnesium stearate, calcium stearate, PEG 6000, sodium stearyl sumarate, sodium lauryl sulphate and mixtures thereof.

13. The dosage form according to claim 12, wherein the lubricant is present in an amount from about 0.2% to 2% by weight.

14. The dosage form according to claim 12, wherein the lubricant is a combination of sodium stearyl fumarate and magnesium stearate.

15. The dosage form according to claim 1, further comprising a solubility enhancer as an extragranular excipient.

16. The dosage form according to claim 1, wherein the intragranular and extragranular binders are independently selected from povidone and hydroxypropyl cellulose.

17. A method for treatment or prophylaxis of an iron-deficiency state, said method comprising administering to a subject in need of said treatment or prophylaxis a dosage form as defined in claim 1.

18. The method according to claim 17, wherein the iron-deficiency state is selected from the group consisting of iron-deficiency anemia, ferropenic anemia, achlorhydria, gastrectomy, burns, excessive blood loss, hemorrhages, renal disease and bowel diseases.

19. An oral pharmaceutical tabletted dosage form prepared by compression with a tableting punch, which comprises a mixture of:
a) granules produced by wet granulation of ferrimannitol-ovalbumin (FMOA), and at least an intragranular pharmaceutically acceptable excipient including an intragranular binder; and
b) extragranular pharmaceutical excipients including an extragranular filler and an extragranular binder,
said extragranular binder being selected from the group consisting of starches, microcrysralline cellulose, povidone, hydroxypropyl cellulose, hydroxyethyl cellulose, hydroxypropylmethyl cellulose and mixtures thereof;
wherein said extragranular binder is present in an amount effective to prevent sticking to said tabletting punch.

20. The oral pharmaceutical tabletted dosage form according to claim 19, wherein said granules are produced by wet granulation of said FMOA and a superdisintegrant with an aqueous solution of said intragranular binder.

21. The oral pharmaceutical tabletted dosage form according to claim 19, wherein said intragranular binder is selected from the group consisting of starches, microcrystalline cellulose, povidone, hydroxypropyl cellulose, hydroxyethyl cellulose, hydroxypropylmethyl cellulose and mixtures thereof.

22. An oral pharmaceutical tabletted dosage form prepared by compression with a tableting punch, which comprises a mixture of:
a) granules comprising ferrimannitol-ovalbumin (FMOA), and at least an intragranular pharmaceutically acceptable excipient including an intragranular binder; and
b) extragranular pharmaceutical excipients including an extragranular filler and an extragranular binder,
said extragranular binder and said intragranular binder each being selected from the group consisting of povidone, hydroxypropyl cellulose, hydroxyethyl cellulose, hydroxypropylmethyl cellulose, and mixtures thereof;
wherein said extragranular binder is present in an amount effective to prevent sticking to said tabletting punch.

23. A process for preparing a dosage form as defined in claim 18, wherein said process comprises:
i) granulating by wet granulation FMOA and at least an intragranular pharmaceutically acceptable excipient including an intragranular binder selected from the group consisting of starches, microcrystalline cellulose, povidone, hydroxypropyl cellulose, hydroxyethyl cellulose, hydroxypropylmethyl cellulose and mixtures thereof;
ii) blending the granules obtained with extragranular pharmaceutical excipients including an extragranular filler and an extragranular binder;
iii) compressing the mixture obtained in the previous step into a tablet; and
iv) optionally, coating the tablet obtained in the previous step,
wherein the extragranular binder is used in an amount of from about 2% to 8% by weight.

24. The process according to claim 23, wherein
i) said granulating comprises:
mixing FMOA 20-30% w/w with mannitol 15-40% and sodium croscarmellose 2-8% w/w;

wetting the thus obtained mixture with an aqueous liquid with a povidone 0.5-8% w/w to obtain a wet powder;

drying the thus obtained wet powder until the water content in the powder is at the most about 5% w/w to obtain granules of a first particulate mixture; and sieving the thus obtained first particulate mixture to obtain a well defined particle size range; and ii) said blending comprises:

adding mannitol 40-60% w/w and hydroxypropyl cellulose 2-8% w/w to said granules of said first particulate mixture to obtain a second particulate mixture; and mixing the second particulate mixture with sodium stearyl fumarate 0.5-2% w/w and magnesium stearate 0.4-1% w/w.

25. An oral pharmaceutical tableted dosage form obtained by the process of claim 23.

26. An oral pharmaceutical tableted dosage form obtained by the process of claim 24.

* * * * *

UNITED STATES PATENT AND TRADEMARK OFFICE
CERTIFICATE OF CORRECTION

PATENT NO. : 9,173,925 B2  
APPLICATION NO. : 13/810346  
DATED : November 3, 2015  
INVENTOR(S) : Ana Isabel Torres-Suarez et al.

Page 1 of 1

It is certified that error appears in the above-identified patent and that said Letters Patent is hereby corrected as shown below:

On the title page, in Item (73)

delete

"Tedee Meiji Farma, S.A."

and insert

-- Tedec Meiji Farma, S.A. --

Signed and Sealed this
First Day of March, 2016

Michelle K. Lee
*Director of the United States Patent and Trademark Office*